United States Patent [19]

Schaefer

[11] Patent Number: 4,534,839
[45] Date of Patent: Aug. 13, 1985

[54] PROCESS FOR THE PHOTOPOLYMERIZATION OF VINYL COMPOUNDS AND PHOTOPOLYMERIZABLE MATERIALS

[75] Inventor: Roland Schaefer, Friedrichsdorf, Fed. Rep. of Germany

[73] Assignee: Kulzer & Co. GmbH, Wehrheim, Fed. Rep. of Germany

[21] Appl. No.: 413,804

[22] Filed: Sep. 1, 1982

[30] Foreign Application Priority Data

Sep. 15, 1981 [DE] Fed. Rep. of Germany ....... 3136484

[51] Int. Cl.³ .............................................. C08F 2/50
[52] U.S. Cl. ........................ 204/159.23; 204/159.16; 430/920; 433/228.1; 523/116
[58] Field of Search ............................ 544/299, 305; 204/159.23, 159.16

[56] References Cited

U.S. PATENT DOCUMENTS

| | | | |
|---|---|---|---|
| 3,932,182 | 1/1976 | Futaki et al. | 544/299 |
| 4,006,023 | 2/1977 | McLaughlin et al. | 524/850 |
| 4,025,704 | 5/1977 | Trevoy | 525/327.6 |
| 4,071,424 | 1/1978 | Dart et al. | 204/159.14 |
| 4,131,729 | 12/1978 | Schmitt et al. | 204/159.23 |
| 4,203,770 | 5/1980 | Grossa et al. | 430/270 |
| 4,273,860 | 6/1981 | Adin | 430/348 |
| 4,282,309 | 8/1981 | Laridon et al. | 204/159.23 |
| 4,351,853 | 9/1984 | Jochum et al. | 204/159.23 |

FOREIGN PATENT DOCUMENTS 2403211  1/1974  Fed. Rep. of Germany.
124594  10/1978  Japan.

Primary Examiner—John C. Bleutge
Assistant Examiner—A. H. Koeckert
Attorney, Agent, or Firm—Frishauf, Holtz, Goodman & Woodward

[57] ABSTRACT

A process for photopolymerization of vinyl compounds and of photopolymerizable materials containing vinyl compounds which is especially useful for dental materials, and compositions useful in said process and the product of said process. The process utilizes a photosensitizer of the formula

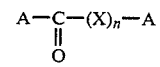

wherein
X is selected from CO, $C(R^1)(R^2)$ or $C(R^3)(OR^4)$,
$R^1, R^2, R^3, R^4$ is selected from hydrogen or a hydrocarbon radical;
n is 0 or 1; and
A are hydrocarbon radicals which may be substituted and which may be bonded together with a proviso that (1) when n is 1 and X is $C(R^1)(R^2)$, and (2) when n is 0, then A is an aromatic radical; and at least one reducing agent of the formula

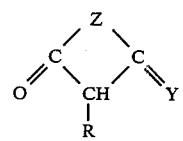

wherein
is selected from O,S or $NR^1$, where $R^1$ is hydrogen or an alkyl group;
Z is an alkylene group with 2 or 3 carbon atoms; wherein one carbon atom can be substituted with one of the heteroatoms O and S or two carbon atoms with at least one of the heteroatoms O,S or N; and
R is a substituted or unsubstituted alkyl or aryl group.

Preferably the photoinitiator is comphorquinone as photosensitizer used with at least one reducing agent selected from the group of 5-alkyl barbituric acid and 5-aryl barbituric acid, preferably 5-butyl barbituric acid or 1-benzyl-5-phenyl-barbituric acid.

9 Claims, No Drawings

PROCESS FOR THE PHOTOPOLYMERIZATION OF VINYL COMPOUNDS AND PHOTOPOLYMERIZABLE MATERIALS

BACKGROUND OF THE INVENTION

The present invention provides a process for the photopolymerization of vinyl compounds in the presence of a photoinitiator.

Photopolymerization has many useful applications in the technical field as, for example, for the curing of lacquers and coatings, in the manufacture of printing plates and in letter press printing.

Photopolymerization is also useful in the dental field as well. Photopolymerizable materials are used in the preparation of dental fillings and sealings, of crowns and bridges and artificial teeth and dentures see, for example, British Pat. No. 569,974 and German Patent Publications Nos. 23 15 645, 23 57 324, 29 10 077 and 29 14 537).

British Pat. No. 1,408,265 describes photopolymerizable materials which contain as a photoinitiator a mixture of:

(a) at least one photosensitizer of the formula

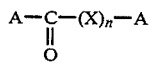

where X is CO, C(R$^1$)(R$^2$) or C(R$^3$)(OR$^4$), R$^1$,R$^2$,R$^3$,R$^4$, which may be the same or different, are hydrogen or hydrocarbyl groups, n is 0 or 1, and the groups A, which may be the same or different, are hydrocarbyl or substituted hydrocarbyl groups and in which the groups A may be further linked together by a direct link or by a divalent hydrocarbyl group, or in which the groups A together may form a fused aromatic ring system, the groups A being aromatic or substituted aromatic (1) when n is 1 and X is C(R$^1$)(R$^2$) and (2) when n is 0, and (b) at least one reducing agent capable of reducing the photosensitizer when the photosensitizer is in an excited state and having the structure

where M is an element of Group V B of the Periodic Table and the units R, which may be the same or different, are hydrogen atoms, hydrocarbyl groups, substituted hydrocarbyl groups or groups in which two units R together with the element M form a cyclic ring system, no more than two of the units R being hydrogen atoms or substituted hydrocarbyl groups and, where element M is attached directly to an aromatic group R, at least one of the other units R has a

group attached to M.

British Pat. No. 1,465,897 discloses photopolymerizable materials useful in dentistry which contain as a photoinitiator a mixture of:

(a) at least one photosensitizer of the formula

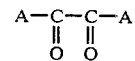

in which the groups A, which may be the same or different, are hydrocarbyl groups or substituted hydrocarbyl groups; and (b) at least one reducing agent capable of reducing the photosensitizer when the photosensitizer is in an excited state and having the formula

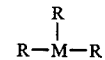

wherein M is an element of Group Vb of the Periodic Table and the units R, which may be the same or different, are hydrogen atoms, hydrocarbyl groups, substituted hydrocarbyl groups, or groups in which two units R together with the element M form a cyclic ring system, no more than two of the units R being hydrogen atoms and the element M not being attached directly to an aromatic group.

The resulting mixtures can be cured by exposure to visible light or through ultraviolet rays. Examples of the photosensitizers include benzil, p,p'-dimethoxy benzil, benzoin, and camphorquinone. Reducing agents include propylamine, dimethylaminoethyl methacrylate, N,N'-dimethylaniline and piperidine.

It is the object of the present invention to provide a photoinitiator having (a) at least one photosensitizer, and (b) at least one reducing agent for the photopolymerization of vinyl compounds which effects a rapid curing and results in good color fastness of the polymerized substance.

SUMMARY OF THE INVENTION

The present invention provides a process for the photopolymerization of vinyl compounds in the presence of a photoinitiator comprising:

(a) a photosensitizer comprising:

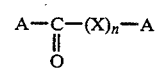

wherein

X is selected from CO, C(R$^1$) (R$^2$) or C(R$^3$)(OR$^4$),
R$^1$,R$^2$,R$^3$,R$^4$ is selected from hydrogen or a hydrocarbon radical;
n is 0 or 1;
A are hydrocarbon radicals which may be substituted and which may be bonded together, with the proviso that (1) when n is 1 and X is C(R$^1$)(R$^2$), and (2) when n is 0, then A is an aromatic radical; and (b) a reducing agent, at least one compound selected from 5-alkyl and 5-aryl-barbituric acids, e.g. 5-butyl and 1-benzyl-5-phenyl-barbituric acid. The photoinitiators composed of camphorquinone and 5-alkyl or 5-aryl-barbituric acids have been proven to be especially advantageous.

The vinyl-polymers and copolymers obtained through the process according to the present invention do not display any discoloration.

The present process is applicable whenever monomer vinyl compounds, especially compositions containing these compounds, are to be photopolymerized by exposure to visible light and/or ultraviolet rays.

The vinyl compounds which may be polymerized in accordance with the present invention include all commonly used ethylene-like unsaturated compounds, especially vinyl chloride and esters of acrylic and methacrylic acids with monohydric and polyhydric alcohols. Also included are the so-called urethane acrylates and methacrylates and Bis-GMA, as shown in U.S. Pat. No. 3,006,112, which is the reaction product of Bis-phenol A and glycidylmethacrylate.

In practice, the photosensitizer is added to the vinyl compounds, especially to the compositions containing these vinyl compounds in an amount of between $10^{-2}$ and 10% by weight, with respect to the vinyl compounds. The preferred amount is between $10^{-1}$ and 5% weight. The reducing agent is also present in the same quantities.

The application of the process according to the invention has been especially beneficial in the field of dentistry, for the preparation of dental fillings and sealings, as well as crowns, bridges and artificial teeth and dentures.

In the following examples photopolymerizable compositions containing vinyl compounds and their polymerization according to the invention are described. The thickness of the resulting solid body of the polymer is measured and serves as the means of comparing the activity of the photoinitiator.

EXAMPLES 1–3

A mixture of
7 g Bis-GMA
3 g triethyleneglycoldimethacrylate
30 g lithium aluminum silicate of fine particle size (85% by weight of the particles with a particle size <15 μm), and
X photoinitiator (see Table 1)
is placed into a small glass tube (inside diameter 6 mm and 30 mm high) which is shielded with aluminum foil in such a way that no light can enter through the sides. The mixture is exposed to the radiation of a tungsten lamp (250W/24V made by Philips) at a distance of 17 cm for a period of 2 minutes.

The portion of the mixture which remained unpolymerized is removed and the thickness of the solid polymer was measured.

Table 1 reports the kind and quantity of the photoinitiator and the thickness of the layer.

TABLE 1

| EXAMPLE | INITIATOR | WEIGHT % | THICKNESS OF LAYER, mm |
|---|---|---|---|
| 1 | CAMPHOR QUINONE | .3 | 3.5 |
| 2 | CAMPHOR QUINONE + 5-BUTYLBARBITURIC ACID | .3 1.0 | >20 |
| 3 | CAMPHORQUINONE + 5-BUTYLBARBITURIC ACID | .3 .2 | 15 |

EXAMPLE 4 (Comparison)

A mixture corresponding to that of Example 2 is placed into a small glass tube (inside diameter 6 mm and 30 mm high) which is completely shielded with aluminum foil, so that upon exposure to radiation none of the radiation can effect polymerization. Thereafter, the small tube is exposed to the radiation of a tungsten lamp (240W/24V made by Philips) at a distance of 17 cm for two minutes. Polymerization of the mixture did not occur.

EXAMPLE 5 (Comparison)

A mixture corresponding to that of Example 2 is placed into a small glass tube (6 mm inside diameter and 30 mm high) and heated to 120° C. for 5 minutes. Polymerization of the mixture did not occur.

EXAMPLES 6–12

A mixture of
9.3 g Bis-GMA,
7.8 g triethyleneglycoldimethacrylate,
6.9 g urethanedimethacrylate, obtained by the reaction of 1 mol of trimethylhexamethylenediisocyanate with 2 moles of 2-hydroxyethylmethacrylate,
23.1 g silicon dioxide, of fine particle size, obtained by high temperature hydrolysis,
2.6 g aluminum oxide, of fine particle size,
50.3 g splinter polymer obtained by the polymerization of a mixture of triethyleneglycoldimethacrylate and silicon dioxide of fine particle size, obtained by high temperature hydrolysis, and
X photoinitiator (see Table 2),
is placed into a small glass tube (6 mm inside diameter and 30 mm high) which is shielded with aluminum foil in such a way that no light can enter through the sides. The mixture is exposed to the radiation of a tungsten lamp (250W/24V made by Philips at a distance of 17 cm for 2 minutes. The portion of the mixture which did not polymerize is removed and the thickness of the layer of the formed body is measured.

Table 2 reports the kind and quantity of the photoinitiator and the thickness of the layer.

TABLE 2

| EXAMPLE | INITIATOR | WEIGHT % | THICKNESS OF LAYER, mm |
|---|---|---|---|
| 6 (COMPARISON) | CAMPHORQUINONE | .2 | 3 |
| 7 (COMPARISON) | CAMPHORQUINONE + N,N'DIMETHYL-p-TOLUIDINE | .2 .2 | 6.6 |
| 8 | CAMPHORQUINONE + METHYLMELDRUM ACID = METHYLMALONIC ACIDISOPROPYLIDENE ESTER | .2 .2 | 5.2 |
| 9 | CAMPHORQUINONE + | .2 | >20 |

TABLE 2-continued

| EXAMPLE | INITIATOR | WEIGHT % | THICKNESS OF LAYER, mm |
|---|---|---|---|
|  | 1-BENZYL-5-PHENYL-BARBITURIC ACID | 1.0 |  |
| 10 | CAMPHORQUINONE | .2 | 19 |
|  | 1-BENZYL-5-PHENYL-BARBITURIC ACID | .2 |  |
| 11 | CAMPHORQUINONE | .2 | >20 |
|  | + |  |  |
|  | 5-BUTYLBARBITURIC ACID | 1. |  |
| 12 | CAMPHORQUINONE | .2 | 15 |
|  | + |  |  |
|  | 5-BUTYLBARBITURIC ACID | .2 |  |

EXAMPLES 13–16

A mixture of
9.3 g Bis-GMA,
7.8 g triethyleneglycoldimethacrylate,
6.9 g urethanedimethacrylate, obtained by the reaction of 1 mol of trimethylhexamethylenediisocyanate with 2 moles of 2-hydroxyethylmethacrylate,
23.1 g silicon dioxide, in fine particle size, obtained by high temperature hydrolysis,
2.6 g aluminum oxide, in fine particle size,
50.3 g splinter polymer obtained by the polymerization of a mixture of triethyleneglycoldimethacrylate and silicon dioxide of fine particle size, obtained by high temperature hydrolysis, and
X photoinitiator (see Table 3)
is placed into a tube (inside diameter 6 mm and 30 mm high) made of Delrin, a polyacetal plastic, and exposed to radiation of a tungsten-halogen visible light fixture Translux made by Kulzer for 20 seconds. The portion of the mixture which did not polymerize is removed and the thickness of the formed body of the polymer is measured.

The kind and quantity of the photoinitiator and the thickness of the layer are reported in Table 3.

TABLE 3

| EXAMPLE | INITIATOR | WEIGHT % | THICKNESS OF LAYER, mm |
|---|---|---|---|
| 13 (COMPARISON) | CAMPHORQUINONE | .2 | 1.7 |
| 14 | CAMPHORQUINONE | .2 | 3.0 |
|  | + |  |  |
|  | 5-BUTYLBARBITURIC ACID | 1.0 |  |
| 15 (COMPARISON) | p,p'-DIMETHOXYBENZIL | .2 | .1 |
| 16 | p,p'-DIMETHOXYBENZIL | .2 | 1.0 |
|  | + |  |  |
|  | 5-BUTYLBARBITURIC ACID | 1.0 |  |

Test specimens with a diameter of 10 cm and a thickness of 2 mm made of photopolymerizable materials according to the invention, as described in the examples, are tested for color fastness in accordance with the standard for dental filling materials ISO 4049. The radiation apparatus used in this test (Suntest) is made by W. C. Hereaus GmbH.

After exposure to radiation and timed according to the standard, the test specimens did not display any visible discolorations.

On the other hand, test specimens employing amines as reducing agents under identical conditions resulted in readily observed discolorations.

In the formula representing the photosensitizer A and $R^1$ to $R^4$ are the same as defined in British Pat. No. 1 408 265.

In the formula representing the reducing agent $R^1$ in $Y=NR^1$ is a hydrogen atom or an alkyl group with 1 to 10 carbon atoms, preferably with 1 to 5 carbon atoms, and R is a substituted or unsubstituted alkyl group with 1 to 10 carbon atoms, preferably with 1 to 5 carbon atoms, or a substituted or unsubstituted aryl group, preferably a phenyl group.

British Patent No. 1 408 265 corresponds to U.S. Pat. No. 4,071,424.

I claim:

1. In a process for the production of a dental composition by the photopolymerization of at least one vinyl monomer in the presence of a photoinitiator, the improvement comprising polymerizing said at least one vinyl monomer in the presence of a photoinitiator, the improvement comprising polymerizing said at least one vinyl monomer in the presence of a photoinitiator comprising:
   (a) camphorquinone as a photosensitizer; and
   (b) at least one reducing agent selected from the group consisting of a 5-alkyl barbituric acid and a 5-aryl barbituric acid.

2. The process of claim 1, wherein the photosensitizer is present in an amount of between 0.01 to 10% by weight based on the weight of the vinyl monomer.

3. The process of claim 2, wherein the reducing agent is present in an amount of between 0.01 and 10% by weight based on the weight of the vinyl monomer.

4. The process of claim 1, wherein said photoinitiator is a mixture of camphorquinone and a 5-alkyl barbituric acid.

5. The process of claim 1, wherein said photoinitiator is a mixture of camphorquinone and a 5-aryl barbituric acid.

6. The process of claim 1, wherein said photoinitiator is a mixture of camphorquinone and 5-butylbarbituric acid.

7. The process of claim 1, wherein said photoinitiator is a mixture of camphorquinone and 1-benzyl-5-phenyl barbituric acid.

8. A photopolymerizable dental material comprising at least one vinyl monomer and a photoinitiator comprising:
   (a) camphorquinone as a photosensitizer; and
   (b) at least one reducing agent selected from the group consisting of a 5-alkyl barbituric acid and a 5-aryl barbituric acid.

9. The photopolymerizable dental material of claim 8, wherein said reducing agent is selected from 5-butyl barbituric acid and 1-benzyl-5-phenyl barbituric acid.

* * * * *